US011013835B2

(12) United States Patent
Ware et al.

(10) Patent No.: US 11,013,835 B2
(45) Date of Patent: May 25, 2021

(54) PROCESSABILITY OF POLYMERIC SUBSTRATES AND RELATED METHODS

(71) Applicant: The Board of Regents of the University of Texas System, Austin, TX (US)

(72) Inventors: Taylor Ware, Beavercreek, OH (US); Walter Voit, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 718 days.

(21) Appl. No.: 14/376,352

(22) PCT Filed: Feb. 3, 2013

(86) PCT No.: PCT/US2013/024547
§ 371 (c)(1),
(2) Date: Aug. 1, 2014

(87) PCT Pub. No.: WO2013/116811
PCT Pub. Date: Aug. 8, 2013

(65) Prior Publication Data
US 2015/0018659 A1    Jan. 15, 2015

Related U.S. Application Data

(60) Provisional application No. 61/594,508, filed on Feb. 3, 2012.

(51) Int. Cl.
| B05D 3/00 | (2006.01) |
| A61L 31/04 | (2006.01) |
| A61L 31/14 | (2006.01) |
| C08J 7/04 | (2020.01) |
| A61B 5/24 | (2021.01) |
| A61L 31/08 | (2006.01) |

(52) U.S. Cl.
CPC .............. *A61L 31/14* (2013.01); *A61B 5/24* (2021.01); *A61L 31/048* (2013.01); *A61L 31/088* (2013.01); *B05D 3/002* (2013.01); *C08J 7/0423* (2020.01); *A61L 2400/16* (2013.01); *A61L 2420/02* (2013.01)

(58) Field of Classification Search
None
See application file for complete search history.

(56) References Cited

U.S. PATENT DOCUMENTS

| 4,020,233 A * | 4/1977 | Morgan | C08G 18/835 |
| | | | 428/419 |
| 5,264,061 A * | 11/1993 | Juskey | H05K 3/0014 |
| | | | 156/214 |
| 5,670,557 A * | 9/1997 | Dietz | A61F 13/023 |
| | | | 522/184 |
| 5,856,022 A * | 1/1999 | McCormick | C08F 265/06 |
| | | | 428/500 |
| 8,927,664 B2 * | 1/2015 | Carlborg | B81C 3/001 |
| | | | 525/535 |
| 2003/0207145 A1 * | 11/2003 | Anderson | B05D 7/14 |
| | | | 428/626 |
| 2006/0066006 A1 * | 3/2006 | Haraldsson | B82Y 10/00 |
| | | | 264/255 |
| 2006/0153990 A1 | 7/2006 | Levey et al. | |
| 2007/0021521 A1 * | 1/2007 | Cheng | C08G 75/045 |
| | | | 522/1 |
| 2007/0073130 A1 * | 3/2007 | Finch | A61N 1/0529 |
| | | | 600/372 |
| 2008/0086113 A1 | 4/2008 | Tenney et al. | |
| 2008/0182081 A1 * | 7/2008 | Jeon | G03F 7/201 |
| | | | 428/195.1 |
| 2010/0040874 A1 | 2/2010 | Narahashi et al. | |
| 2010/0152410 A1 | 6/2010 | East et al. | |
| 2010/0218716 A1 | 9/2010 | Havens et al. | |
| 2010/0298895 A1 * | 11/2010 | Ghaffari | A61B 1/00082 |
| | | | 607/3 |
| 2010/0308204 A1 * | 12/2010 | Taniguchi | C23C 4/185 |
| | | | 249/114.1 |

OTHER PUBLICATIONS

Carlborg, Carl Fredrik, Tommy Haraldsson, Kim Öberg, Michael Malkoch, and Wouter Van Der Wijngaart. "Beyond PDMS: off-Stoichiometry Thiol-Ene (OSTE) Based Soft Lithography for Rapid Prototyping of Microfluidic Devices." Lab on a Chip 11 (18) (Year: 2011).*

* cited by examiner

*Primary Examiner* — Jose I Hernandez-Kenney

(57) ABSTRACT

The invention discloses a method for adhering a metal layer to a polymer substrate. The metal layer is deposited on a sacrificial substrate of a mold to form part of an interior surface of the mold, and a solution of monomers is deposited on the metal layer. The monomers are then polymerized together to form the polymer substrate on the metal layer. Then the polymer substrate is removed from the mold such that the metal layer is removed from the mold and adhered to the polymer substrate.

12 Claims, 4 Drawing Sheets

PROCESSABILITY OF POLYMERIC SUBSTRATES AND RELATED METHODS

CROSS-REFERENCES TO RELATED APPLICATIONS

This application claims the benefit under 35 U.S.C. § 119(e) of U.S. Provisional Patent Application Ser. No. 61/594,508, filed Feb. 3, 2012, which is incorporated herein by reference in its entirety as if fully set forth herein.

STATEMENT REGARDING FEDERALLY-SPONSORED RESEARCH OR DEVELOPMENT

This invention was made with government support under Grant No. 2011113646 awarded by the National Science Foundation and with FUSION support from the State of Texas. The government has certain rights in the invention.

BACKGROUND OF THE INVENTION

Thin films of conductive and/or decorative metals, particularly transition metals or their alloys, can be only selectively applied to polymeric substrates or coated with polymeric films because of the lack of adhesion of most metals to polymers. In general, the surface of the polymer must be modified, as by oxidation, roughening, or the like, or an intermediate adhesion-promoting agent must be applied to the polymer or metal surface which adds to the cost and sometimes detracts from the appearance of such laminates. The use of films as decorative and durable coatings would increase if a method could be found to coat polymeric substrates with strongly adherent, metallic or conducting films, particularly in the area of flexible electronics, biomedical devices and neural electronics.

Flexible electronics have become important in recent years. In particular, flexible electronics can be important because it allows the integration of high performance electronic devices to several fields of application where typical electronics on rigid substrates could not be integrated. Flexible electronic devices can be easily integrated on several kinds of curved surfaces. For example, within the healthcare sector, electronic devices and circuits developed on flexible substrates can be exploited to monitor, for example, glucose blood level, temperature, pressure, etc. In such a way, electronic plasters, implantable sensors, etc., can be developed. The method and devices developed with the same may enable such sensors developed on a flexible substrate to be minimally invasive and more easily accepted by the patient since they are better adapted to the shape and mechanical properties of the human body than typical electronic devices and systems. Other application fields include ambient intelligence, distributed sensors, electronics on textiles, energy harvesting, power management, and industrial electronics.

A potential issue relating to flexible electronics concerns the fabrication of flexible electronic devices. In particular, the fabrication of flexible electronic devices may be critical because it involves the handling of flexible, and thus fragile, electronic/semiconductor devices. Accordingly, the fabrication of flexible electronic devices is costly since it involves the employment of special handling and packaging tools suitable for handling flexible semiconductor devices without damaging them.

Cortical neural interfaces provide a communication platform for direct interaction with the nervous system. Communication with the central nervous system has enabled treatment of numerous conditions such as epilepsy and depression, control of prosthetic devices and the advancement of the field of neuroscience. However, devices designed to record extracellular neural activity generally fail within one year of implantation. This failure has been widely attributed to gliosis, the chronic reactive biological response to the foreign probe, which leads to death of neurons and encapsulation of the implant resulting in a loss in the signal-to-noise-ratio or the inability to invoke responses through stimulation over time. A number of factors contribute to the timeframe and extent of the observed gliosis: size, stiffness, surface chemistry, insertion procedure and mechanical constraints provided by electrical contacts have been shown to have a direct effect on glial scarring. The focus of this work is to minimize long term device stiffness, but each parameter must be considered in device development.

Neural interfaces are typically made of silicon microneedles, planar electrodes or metal microwires. The extreme mechanical mismatch between these devices (commonly tungsten or silicon) is strongly linked to the extensive gliosis and reduction in signal quality over time. Recently much research has focused on the design, manufacture and implantation of flexible probes made from polymers, such as polyimides or Parylene-C, with thin-film conductors defined by photolithography; these devices have a reduced mechanical mismatch between neural tissue and the implants. Polymer probes are stiff enough for implantation into the cortex directly or with the aid of an insertion tool, depending on geometry. These polymers are still, however, 5 or 6 orders of magnitude stiffer than the surrounding neural tissue. Softening neural interfaces have been demonstrated utilizing the swelling of a nanocomposite polymer film. Combining advances in polymer-based probes and shape memory polymers (SMPs) will allow for the further development of devices that are stiff enough for insertion, but undergo orders-of-magnitude reduction of stiffness following insertion.

SMPs are a class of mechanically active materials used to store a metastable shape and return to a globally stable shape upon activation by a stimulus, such as temperature, humidity, light or a combination of these stimuli. In thermally active SMPs, recovery is induced by heating the polymer through a transition, such as crystalline melting or a glass transition, leading to a considerable drop in modulus. SMP activation by moisture is a variation of thermal activation, where the drop in modulus is triggered by plasticization of the polymer leading to thermal activation at a lower temperature. Many thermally activated SMP biomedical devices have been proposed including cortical probes that self-insert upon recovery of the device. Research in flexible electronics has produced neural interfaces on flexible substrates such as, Parylene-C, various polyimides and other engineering thermoplastics, and soft, elastomeric substrates. Processing by photolithography on shape memory polymer substrates that demonstrate a dramatic change, from flexible to soft, triggered by physiological conditions has not been studied extensively.

SUMMARY OF THE INVENTION

The invention described herein discloses a method for adhering a metal layer to a polymer substrate. The method comprises depositing the metal layer on a sacrificial substrate of a mold to form part of an interior surface of the mold and depositing a solution of monomers on the metal layer located on the interior surface of the sacrificial substrate of the mold. The method comprises then polymerizing the monomers together to form the polymer substrate on the metal layer and then removing the polymer substrate from the mold such that the metal layer is removed from the mold and adhered to the polymer substrate. In some embodiments, the metal layer includes a layer of gold, iridium oxide, titanium nitride, or titanium oxide and, in some such embodiments, the metal layer includes the layer of gold located on a layer of aluminum, chromium or titanium. In some embodiments, the polymerizing of the monomers together forms the polymer substrate that is a thiol-ene, urea, thiourethane, or olefin polymer. In some embodiments, the metal layer of the mold is lithographically patterned prior to the depositing of the solution of monomers on the metal layer of the mold. In some embodiments, the mold is a blend of radiation crosslinked thermoplastic polymer and a polyunsaturated monomer, or, an epoxy or siloxane. In some embodiments, the polymerizing of the monomers together to form the polymer substrate includes forming a partially polymerized polymer substrate. In some embodiments, the partially polymerized polymer substrate is deformed into a different shape, and then, the polymerizing of the monomers together to form the polymer substrate is completed. In some embodiments, the solution of monomers includes methyl acrylate and isobornyl acrylate crosslinked with poly(ethylene glycol)diacrylate and in some such embodiments, wherein the solution of monomers further includes a co-monomer of 2-hydroxyethyl acrylate, 2-hydroxyethyl methacrylate (2HEMA), acrylic acid or mono-2-(Methacryloyloxy)ethyl succinate. In some embodiments, the solution of monomers further includes a co-monomer of acrylic acid. In some embodiments and in some such embodiments, the acrylic acid in the solution of monomers is in a concentration range from 10 wt % to 20 wt %.

DETAILED DESCRIPTION OF EXEMPLARY EMBODIMENTS

Figure 1:
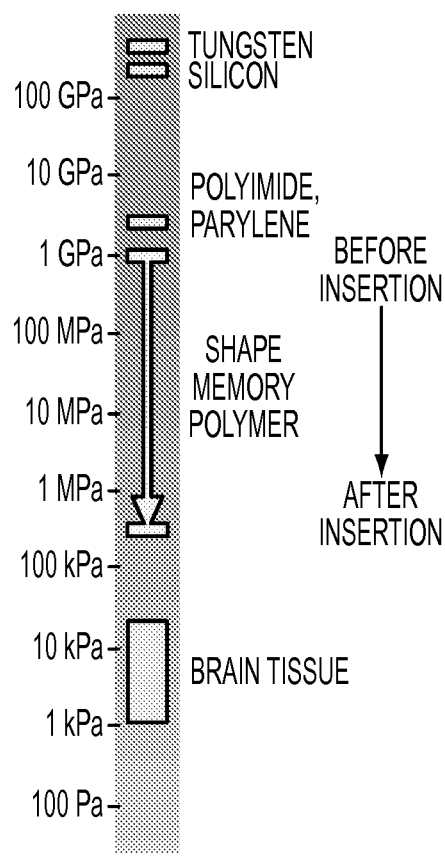
FIG. 1 shows a schematic drawing that illustrates the modulus range of polymer systems in accordance with embodiments of the claimed invention.

The invention described herein consists of a process that enables increased adhesion of thin film materials (such as metals, metal oxides, carbon nanotubes or other materials) to solvent and temperature sensitive, and non-planar, polymer substrates and the fabrication of softening electronics. Importantly, this process can be used to create exceptional embodiments of the disclosed flexible electronic devices having dynamic properties that make them suitable for implantation in the human body.

The invention described herein consists of a process that enables increased adhesion of materials (such as metals, metal oxides, carbon nanotubes or other materials) to solvent and temperature sensitive, and optionally non-planar, polymer substrates. This increased adhesion arises due to the interaction of polar functional groups in the polymer substrate to an oxide that is present on the surface of the exposed film material or from the interaction of metals with specific adhesion-promoting chemistries such as thiol or thioether groups. The process described by the invention involves three steps. 1) The first is the sputtering, deposition, curing, growth or the like of metals, nanotubes or other conducting materials or ceramics, semiconductors, piezoelectrics or thermoelectrics onto a sacrificial substrate of one or several materials. The exposed surface after deposition serves as an eventual adhesion layer between the polymer substrate and optionally any other deposited materials that will be utilized to bestow some functionality on the device after further processing. This adhesion layer must have a strong affinity for the polymer substrate. 2) A monomer solution is polymerized, or a resin is cured, in a mold constructed at least partially of the previously deposited film material(s). 3) The polymer substrate is removed from the mold and the adhesion between the polymerized substrate and the film is sufficient to transfer the material(s) from the sacrificial substrate to the desired substrate. The result is a film coated (e.g. metalized) substrate with enhanced adhesion between the material(s) and the polymer substrate. These composite materials could be able to withstand environments and loads that would cause similar composites made by direct metal deposition onto the flexible substrate or other means to fail by delamination or other methods. This method also allows transfer with enhanced adhesion of photolithographically patterned structures to substrates that show drastic changes in properties in response to temperatures often reached in processing (0-100° C.) or the presence of solvents (water, acetone, isopropanol, methanol, ethanol, toluene etc.). Traditional methods do not allow for patterning of film structures on these dynamic substrates. The ability to pattern electronics on dynamic substrates enables the incorporation of lithographically defined structures on shape memory polymers that can change stiffness and/or shape in response to stimuli such as temperature and presence of water or other small molecules.

One embodiment is a method for improving the adhesion of films to polymeric materials comprises depositing a first layer of metals, nanotubes or other ionic or electronic conducting materials such as but not limited to iridium oxide, titanium nitride, titanium oxide or graphene oxide, or combinations of the materials onto the surface of a first substrate to prepare a mold; preparing and depositing, solvent casting, or polymerizing a second layer comprised of a polymer on the first layer within the mold; and removing the polymer coated layer from the mold such that the thin film material layer is removed from the first substrate and transferred to the polymer layer which serves as a second substrate. In some embodiments, the first layer comprises gold and in some such embodiments, the first layer further comprises chromium or titanium. The some embodiments, the polymer is a (meth)acrylate, thiol-ene, urea, urethane, thiourethane, ester, or olefin with or without an initiator or catalyst. In some embodiments, the first layer is patterned prior to the deposition of the second layer. In some embodiments, the first substrate is made from the radiation cross-linking of blends of a thermoplastic polymer and a polyunsaturated monomer. In some embodiments, the first substrate is formed by curing epoxy. In some embodiments, the first substrate is formed by curing siloxane. In some embodiments the substrate is partially cured to prepare a three dimensional mold or a different two-dimensional permanent mold from the initial transfer. In some embodiments, the substrate is completely cured. In some embodiments, the polymer is functionalized to promote attachment to other molecules such as neural attachment molecules or anti-biofouling molecules. In some embodiments, the first layer and any subsequent layers are patterned into devices such as transistors, capacitors, resistors, inductors, or diodes such as organic light emitting diodes, prior to the deposition of the transfer polymeric layer.

One embodiment is a device fabricated on a shape memory polymer substrate, wherein the device softens and/or changes shape upon exposure to a physiological environment. In some embodiments, the physiological environment is the human brain or the spinal cord. In some embodiments, the device comprises thiol-ene/acrylates, thiol epoxies, thiol-enes, thiourethanes, acrylates, ureas, urethanes or combinations thereof. In some embodiments, the device is a flexible electronic device. In some embodiments, the device is an intracortical electrode array, inferior colliculus implant, deep brain stimulator, electrocorticography array, spinal cord electrode or brain stem implant. In some embodiments, the device is used in a peripheral nervous system neural interface. In some embodiments, the device interfaces with the cardiovascular system, nervous system, lymphatic system, pulmonary system, endocrine system, or musculoskeletal system. In some embodiments, the device is softened by either plasticization of the polymer substrate or hydrolysis of the polymer substrate or both. In some embodiments, the modulus decreases by 2 to 4 orders of magnitude upon exposure/insertion into the physiological environment. In some embodiments, Young's modulus of the device decreases to less than 10 MPa.

An embodiment of the claimed invention is directed to a process comprising the step of depositing a first gold layer by physical vapor deposition onto a sacrificial substrate such as glass, silicon or a polymer. The adhesion of metals such as gold to these substrates is known to be poor. Following the deposition of gold, the next deposited layer is a metal such as chrome or titanium which has been shown to adhere to gold and spontaneously forms an oxide when exposed to air. At this point, if desired, lithography or other patterning techniques can be used to pattern the film metal(s). A mold is constructed using the sacrificial substrate with the adhesion layer of the metal forming some part of the interior surface of the mold. The mold is filled with a monomer solution, such as a liquid (meth)acrylic copolymers, with a free radical initiator and polymerized through ultraviolet radiation or heat. The sacrificial substrate can be removed after the reaction has run to sufficient completion and the metal will be transferred to the poly(meth)acrylic substrate. (Meth)acrylic monomers are of potential interest due to the presence of polar ester bonds in every repeating unit of the polymer and the wide variety of mutually miscible monomers many of which contain further polar groups. These polar groups, when polymerized directly onto a polar substrate such as chromium, titanium, aluminum or the oxides of these materials, provide increased adhesion between the polymer and the metal.

A further embodiment of the invention is directed to a process comprising the step of depositing a gold, silver or platinum layer by physical vapor deposition onto a sacrificial substrate such as glass, silicon or a polymer. The adhesion of metals such as gold, silver and platinum to these substrates is known to be poor. These metals are however known to adhere well to sulfur-containing compounds including thiols and thioethers. At this point, if desired, lithography or other patterning techniques can be used to pattern the film metal(s). A mold is constructed using the sacrificial substrate with the adhesion layer, which in this case consists of gold, silver, or platinum, of the metal forming some part of the interior surface of the mold. The mold is filled with a liquid thiol-ene monomer solution with optionally a free radical initiator and polymerized through ultraviolet radiation or heat. Thiol-ene monomer solutions include any combination of di- or multi-functional thiol containing monomers with monomers containing di- or multi-functional vinyl monomers capable of polymerizing with thiol functionalities by radical mechanism or Michael-type addition. The sacrificial substrate can be removed after the reaction has run to sufficient completion and the metal will be transferred to the substrate. Thiol-ene reactions can be controlled in a way such that the conversion of thiol groups or vinyl groups is incomplete allowing for improved adhesion due to the presence of free thiol groups. Specifically this can be achieved by reacting thiols stoichiometrically with (meth)acrylates, or using a stoichiometric imbalance of vinyl monomers to thiols. In addition to electrode adhesion, these residual functionalities can be used to covalently adhere desired molecules, such as bioactive molecules, to the polymer surface after metal transfer.

Additional embodiments of the invention are directed to the use of mutually miscible monomers or monomers in a polymerization in the presence of a solvent of diluent to form chemistries distinct from the meth(acrylic) and thiol-ene systems. Examples of these distinct chemistries include polyurethanes, polyureas, epoxies, systems all of vinyl polymers or other polymer chemistries. It is important to note that not all examples of these chemistries will be applicable as the removal of certain polymerization solvents may not allow for the polymer to adhere to the metal.

Another embodiment consists of a similar process involving a substrate made from the radiation crosslinking of blends of a thermoplastic polymer and a polyunsaturated monomer. Another embodiment consists of directly curing an epoxy system as the substrate. Another embodiment consists of curing a siloxane as the soft substrate. A further embodiment is directed to curing the substrate to enable transfer and subsequently further deforming the substrate to enable three dimensional shapes before curing, polymerization and/or crosslinking are complete. In an embodiment of the invention, the substrate is partially cured. In another embodiment of the invention, the substrate is fully cured.

Materials (such as thin film metal) transfer to non-planar substrates with the enhanced benefits of adhesion and functionalization is described herein. This distinction arises if the polymer film is allowed to react sufficiently to form a film capable of transferring the material from the sacrificial substrate, but not to completion. This can be achieved by limiting the reaction time. The partially-reacted film is subsequently deformed, and the reaction is completed. The substrate maintains this non-planar geometry as its globally stable shape. The adhesion of many materials particularly gold, silver, platinum, silicon carbide or silicon nitride to various substrates has traditionally been very poor. Current solutions use adhesion layers such as thin film chromium and titanium to promote the adhesion of other metals or ceramics to a wide variety of substrates, especially silicon. This solution has been applied directly to work on flexible polymeric substrates with poor results. Numerous techniques have surfaced to confront this problem mainly focusing on ways to increase the mechanical bonding between the thin film and the substrate. This method utilizes the inherent chemical structure of many polymers to provide an enhanced chemical bonding between metal and substrate. The mechanical bonding of the two substrates is at least on par with current methods as the polymer conformally forms on the surface roughness of the oxide of the adhesion layer. The improved adhesion between the material, such as a thin film metal and substrate will allow for the device to withstand loads and environments that would otherwise cause failure. Further selection of polymer substrates may allow for the removal of the adhesion layer or the utilization of more stretchable adhesion layers which may be of use for stretchable electronics as the failure strain of gold is much higher than that of titanium or chrome.

The claimed invention also allows for a new class of temperature and/or solvent sensitive and optionally non-planar polymeric substrates. Lithography and other potentially substrate damaging processes can be performed before the metal or ceramic has been transferred to the final substrate. This allows well developed electronics processing methods to be utilized while bestowing the final device the highly desirable properties of many smart polymer substrates. Current procedures of production for the metallization (and subsequent device patterning) on polymeric substrates are all completed on a polymerized polymer film. The claimed invention integrates the synthesis of the substrate with the manufacture of the device (metallization of the substrate) in a way that is both novel and beneficial to the properties of the final device. This invention utilizes in a way not previously possible the chemical structure of the polymer and the thermodynamic tendency of the system to minimize the free energy of the surface and as such increase the adhesion of the polymer to the film metal. Surprisingly this process also allows for the adhesion of lithographically patterned metal structures to substrates once deemed incompatible with this process. This invention differentiates itself from the known prior art in that the polar groups are inherent to the polymer, these groups align in the highly mobile monomeric state and in that much of the manufacturing process occurs on a sacrificial substrate. There are several applications utilizing this process that are in the working prototype stage (multi-electrode arrays on an poly(meth) acrylate and thiol-ene based substrates for use as in-vitro or in-vivo neural recording device).

An embodiment of the invention is directed to a cortical probe that is fabricated on an SMP specifically tuned to soften following exposure/insertion into the human body and specifically, the brain. These softening probes behave similarly to current generation flexible probes during exposure/insertion and soften to behave as an elastomer after exposure/insertion. This concept is demonstrated schematically in FIG. 1. Such a process is necessary for the patterning of microelectrodes and s important to enable development of reliable high density interfaces. Furthermore, coupling SMP substrates and these design paradigms with the inventive process to enhance adhesion builds a foundation upon which a variety of robust, self-softening, flexible biotechnology devices can be fabricated.

In an embodiment of the invention, a thermally and water sensitive SMP system is synthesized and characterized based on commercially-available acrylate monomers. A modular transfer-by-polymerization process to fabricate highly reproducible, robust electrodes for interfacing with cortical tissue on these physiologically active SMPs was developed. All features were produced with photolithography allowing high electrode count with small and precise features on a variety of different substrates. The process is designed to enhance chemical and mechanical interactions between a lithographically defined Au/Cr electrode and the tailored polymer system to improve metal-polymer adhesion. (Meth)acrylate polymers inherently contain both hydrophobic and hydrophilic components; this is utilized to tailor thermomechanical properties in physiological conditions and the metal-polymer interaction.

Embodiments of the claimed invention are directed to products and devices made from the inventive processes set forth and described in the instant application. Examples of these devices include electronic devices that can be implanted in the human body. Embodiments of the claimed invention are directed to products made using thiol-ene/acrylates, thiol-epoxies, thiol-enes, thiourethanes, acrylates, ureas, urethanes and combinations thereof. Products produced by the processes of the claimed invention can be used in several applications including, but not limited to, flexible electronics substrates for use in central nervous system neural interfaces and peripheral nervous system neural interfaces. In certain embodiments of the invention, the substrates are processed using photolithography methods. In other embodiments of the invention, the substrates are processed using shadow masking techniques.

Examples of uses of the products produced by the inventive process of the claimed invention in central nervous system neural interfaces include intracortical electrode arrays (motor cortex, somatosensory cortex, auditory cortex, visual cortex), inferior colliculus implants, deep brain stimulators, electrocorticography arrays, spinal cord electrodes and brain stem implants. Examples of uses of the products produced by the inventive process of the claimed invention in peripheral nervous system neural interfaces include nerve cuff electrodes, vagus nerve electrodes, dorsal root ganglion electrodes, intrafascicular electrodes, regenerative electrode arrays, electromyography arrays, cochlear electrodes. Additionally, the products produced by the inventive process of the claimed invention include devices that interface with the cardiovascular system, nervous system, lymphatic system, pulmonary system, endocrine system, musculoskeletal system.

An embodiment of the invention is directed to implantable electronics that exhibit softening properties following implantations. In certain embodiments of the invention, the softening properties are achieved by plasticization of the polymer substrate. In other embodiments of the invention, the softening properties are achieved by hydrolysis of the polymer substrate. In certain embodiments of the invention, the softening of the polymer substrate is achieved through hydrolysis of cleavable linkages in the polymer substrate.

In certain embodiments of the invention, the softening properties are achieved by a combination of hydrolysis and plasticization of the polymer substrate. In certain embodiments of the invention, the polymer substrate is a thermoset (crosslinked) polymer. In other embodiments of the invention, the polymer substrate does not contain polyvinyl acetate.

In an embodiment of the invention, softening substrates are used for flexible electronics which do not cause cracking or delamination of thin film materials as a result of processing at temperatures through or above the glass transition temperature.

In certain embodiments of the invention, the polymer substrate is softened upon exposure to a physiological temperature. Such an exposure can be insertion or implantation in a physiological environment. Such softening is achieved through plasticization of the polymer substrate coupled with fluid uptake ranging from 1 wt % to less than 30 wt %. In specific embodiments, the fluid uptake is less than 20 wt %, or more specifically less than 10 wt %. In other embodiments, the fluid uptake is less than 5 wt %, or more specifically less than 3 wt %.

An embodiment of the invention is directed to electronics exhibiting softening properties having a minimum patterned thin film feature size ranging from 5 μm to less than 100 μm. In specific embodiments, the thin film minimum feature size is less than 50 μm, or more specifically less than 20 μm. In other embodiments, the thin film minimum feature size is less than 10 μm. In yet other embodiments, the thin film minimum feature size is less than 5 μm, or less than 2 μm.

In certain embodiments of the invention, devices made from polymer substrates soften by at least a half order of magnitude upon exposure/insertion to a physiological environment. In other embodiments of the invention, devices made from polymer substrates soften by 2 to 4 orders of magnitude upon exposure/insertion into a physiological environment.

In certain embodiments of the invention, implantable devices having an initial modulus of greater than 100 MPa are softened (i.e., lowered) to a modulus below 50 MPa, upon implantation in physiological conditions. In certain embodiments of the invention, the initial modulus of the implantable device is greater than 250 MPa and preferably greater than 1000 MPa. In other embodiments of the invention, the modulus of the device is softened to less than 25 MPa, less than 10 MPa or preferably less than 0.25 MPa.

In accordance with the transfer-by-polymerization process described in the instant application, a physiological responsive substrate is synthesized to form neural recording devices that are rigid during processing and exposure/insertion and soft after implantation; and to fabricate and incorporate high-density electrodes onto these substrates in a way that fully utilizes the available functional groups in the underlying substrate to provide a robust bond between the deposited materials and the polymers. Process engineering for devices with tunable substrate properties requires simultaneous consideration of the substrate synthesis, device fabrication, application requirements and environment. A substrate designed to soften in physiological conditions with the onset of the dry glass transition above 45° C., was selected to allow electrode definition using photolithography.

Figure 2A:
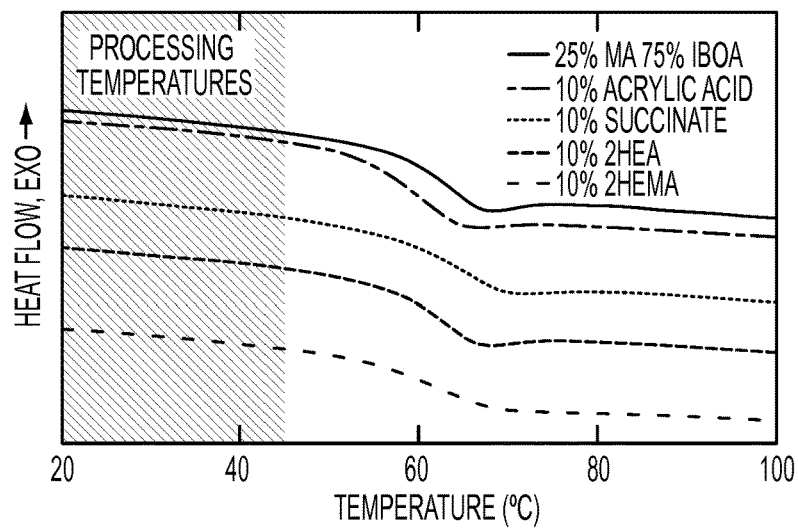
FIG. 2 shows differential scanning calorimetry (DSC) of several compositions containing different hydrophilic monomers (FIG. 2A); Dynamic mechanical analysis (DMA) of the same compositions shown in FIG. 2A before swelling (FIG. 2B); and Post-swelling DMA of the compositions characterized in FIGS. 2A and 2B (FIG. 2C), in accordance with embodiments of the claimed invention.
Figure 2B:
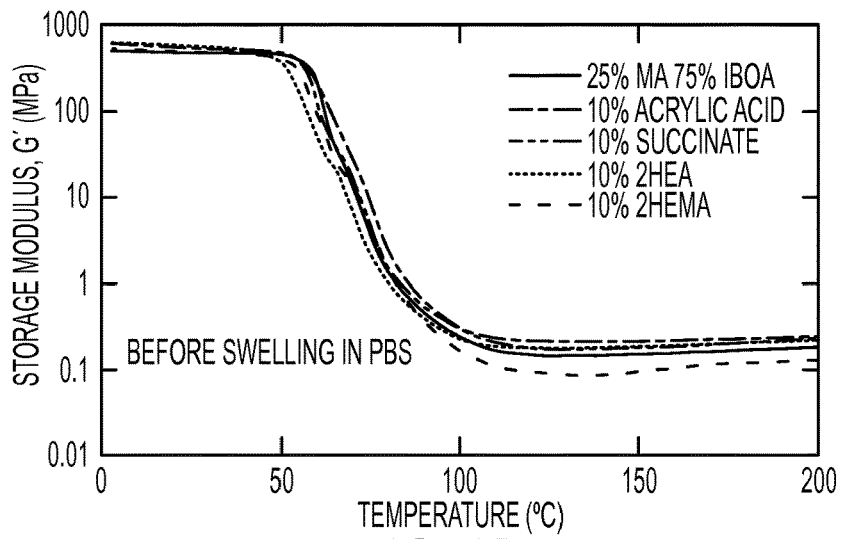
Figure 2C:
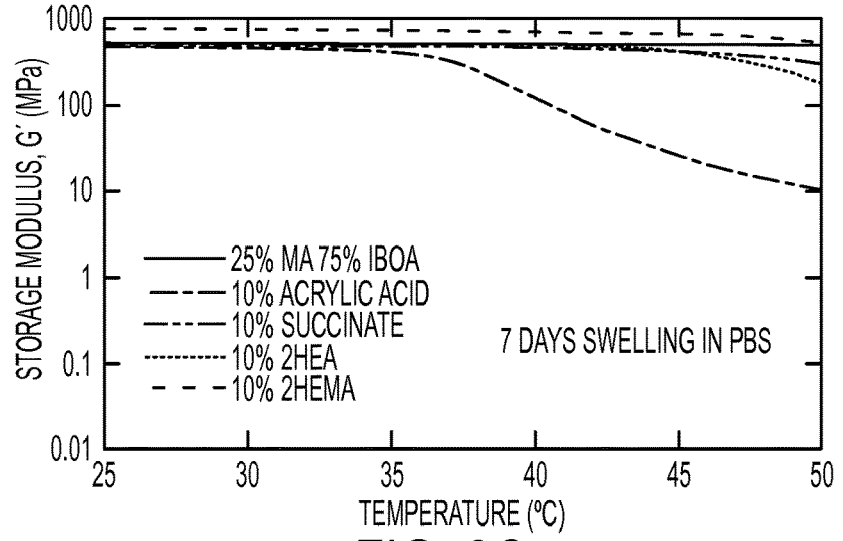

In an embodiment of the invention, a system comprised of monomers methyl acrylate (MA) and isobornyl acrylate (IBoA) crosslinked with 1 wt % poly(ethylene glycol) diacrylate was copolymerized in varying concentrations to control the glass transition temperature ($T_g$) and maintain hydrophobicity of the resulting substrates. The ratio of MA and IBoA was tuned such that the onset of the glass transition would be 60° C. Additionally, a set of other comonomers was screened to increase the hydrophilic nature of the network; 10 wt % comonomer was chosen to evaluate the efficacy of each potential new substrate at softening in physiological conditions. 2-hydroxyethyl acrylate (2HEA), 2-hydroxyethyl methacrylate (2HEMA), acrylic acid (AA) and mono-2-(Methacryloyloxy)ethyl succinate (succinate) each contain hydroxyl groups or carboxylic acids. These groups when incorporated into acrylic copolymers have been shown to increase the hydrophilic behavior in the system. The $T_g$ of each composition was tuned according to the effect of each comonomers to be equal to that of the base composition 25 wt % MA, 75 wt % IBoA. Differential scanning calorimetry (DSC) and dynamic mechanical analysis (DMA) of the five selected samples, while dry, is shown in FIGS. 2A to 2B. Each network exhibits largely similar thermomechanical properties with the $T_g$ of each sample by both DMA and DSC varying by less than 5° C. It should be noted that the shear storage modulus at body temperature is very similar for each sample (~700 MPa). These samples were swollen in phosphate buffered saline for 1 week and retested by DMA. FIG. 2C indicates that the sample containing 10 wt % acrylic acid (AA) undergoes significant plasticization. Other hydrophilic comonomers did not have the same magnitude of effect as AA. DMA on swollen materials was not performed while the sample was immersed in PBS but immediately after removal.

Due to the enhanced softening effect of substrates copolymerized with AA, further samples were synthesized containing between 10 wt % and 20 wt % AA using a fixed percentage of MA (40 wt %) that positioned the $T_g$ near 60° C. for 10 wt % AA and replacing IBoA with AA directly for samples containing greater than 10 wt %. For dry samples, $T_g$ by DSC slightly increases with AA content. DMA is consistent with the DSC and shows the modulus drop associated with $T_g$ is largely the same for each composition. No significant drop in modulus at physiological temperature (indicated by markers on each curve) is observed over 1 day for the control or 10 wt % AA sample. Polymerizing 15 wt % AA into the MA-IBoA copolymers yields a drop in modulus of approximately 1 order of magnitude upon immersion in PBS. Incorporating 17.5 wt % and 20 wt % AA monomers each yields a drop in modulus of approximately 2 orders of magnitude.

Figure 3A:
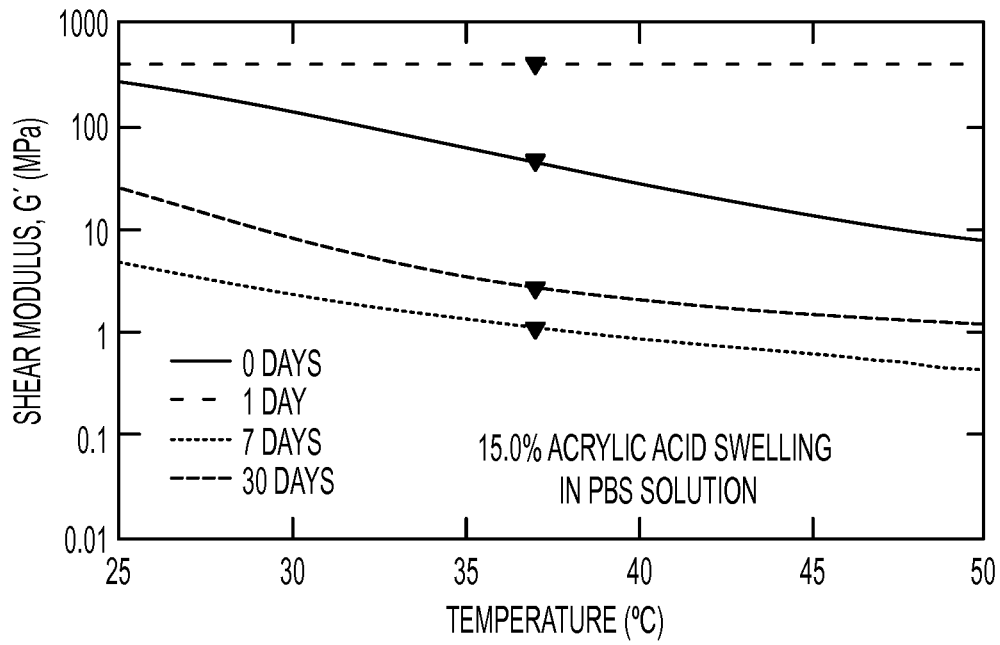
FIG. 3 shows DMA of polymer samples after swelling in PBS solution in accordance with embodiments of the claimed invention.
Figure 3B:
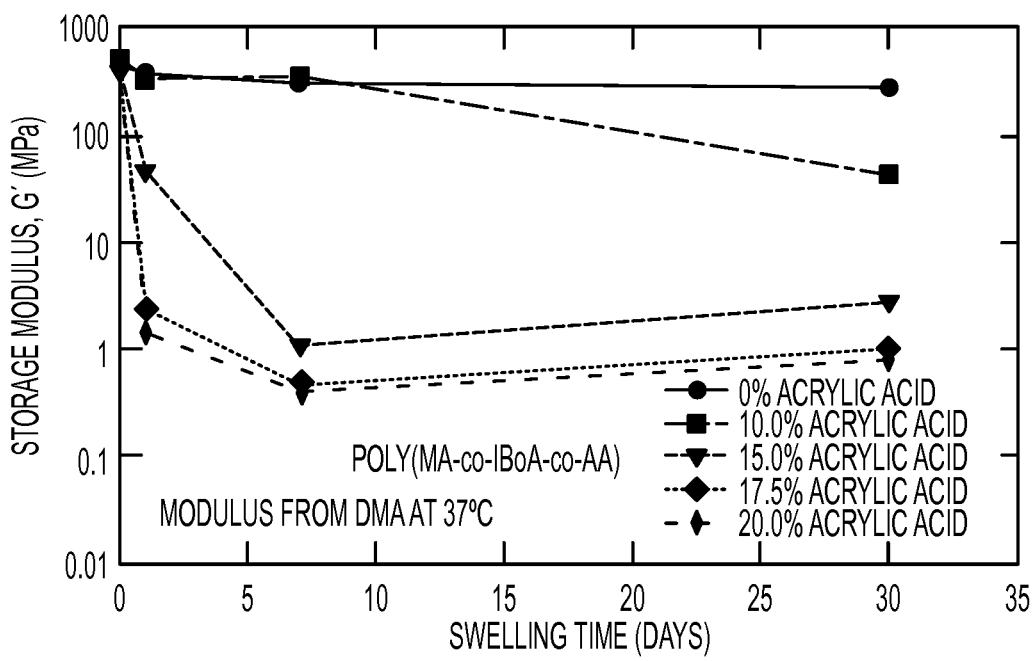

FIG. 3A shows the progression of the modulus drop of the 15 wt % AA sample over 1 month of immersion in PBS. Immersion causes a decrease in modulus of larger than 2 orders of magnitude over 1 week and a slight increase in modulus at 1 month. FIG. 3B shows the evolution of the body temperature modulus for the control and 4 AA-containing samples over 1 month. For samples containing greater than 10 wt % AA, each sample softens significantly over 1 week and shows slight stiffening between 1 week and month. The control sample softens very little over this time period, and the 10 wt % AA sample softens approximately 1 order of magnitude. The control substrate and the 4 AA-containing substrates were chosen for device fabrication and process characterization.

Figure 4A:
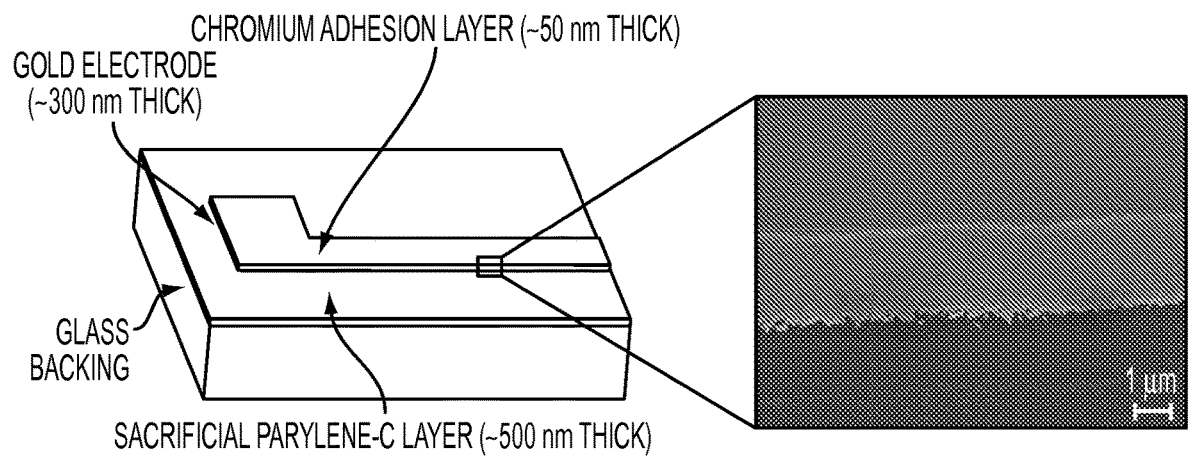
FIG. 4 shows the process schematics and images demonstrating the transfer-by-polymerization process in accordance with embodiments of the claimed invention.

Photolithography often requires and exposes the substrate to organic solvents, water, heat, vacuum, bases and acids. It also requires that the adhesion between thin films and substrates be sufficient for processing, and that the substrate not deform sufficiently, by mechanical means or from thermal expansion, to crack the often fragile thin films. The polymer substrates used herein are sensitive to many of these conditions and process control is crucial. To overcome these challenges a transfer-by-polymerization is described. Parylene-C was deposited on a large clean microscope slide to serve as a sacrificial substrate. On this sacrificial substrate, gold and then a chromium adhesion layer were deposited and patterned using electron-beam deposition, photolithography and subsequent wet etching. FIG. 4A shows, schematically and with SEM, a portion of the substrate in this step. Using this glass slide as the bottom of a mold consisting of another clean glass slide and a spacer of the desired thickness, a mold is constructed. The mold is then filled with the monomer solution and polymerized with 365 nm UV light. After polymerization, the Parylene-C sacrificial layer and electrodes are transferred to the SMP substrate. This is enabled by the poor adhesion of Parylene-C to glass. The device is flipped over, removed from the mold and the sacrificial layer of Parylene-C is removed by reactive ion etching (RIE) with oxygen plasma.

Figure 4B:
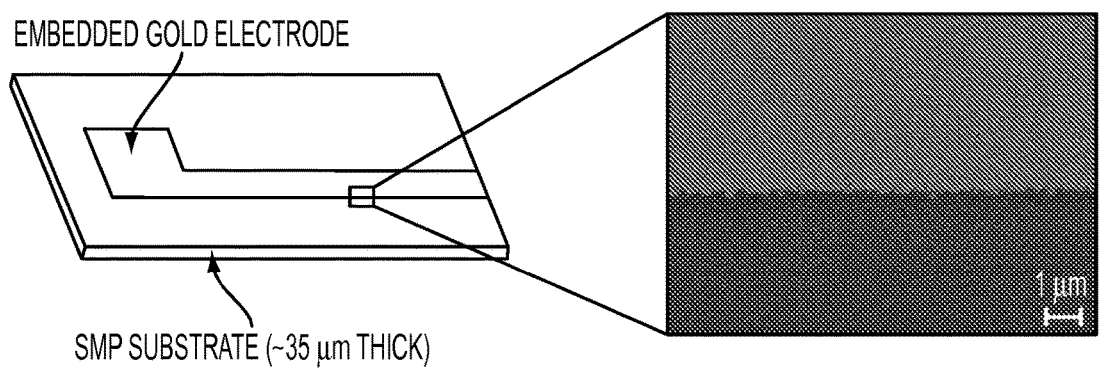

The sample in this stage is shown in FIG. 4B. It should be noted that the gold is now exposed and the top plane of the electrode is shared with the surface of the polymer. The sample is then recoated with a new layer of Parylene-C to insulate the devices with a pinhole free coating. Using photolithography, recording sites and electrical contacts are patterned and opened using RIE.

Metal film adhesion to the SMP substrate is measured by a tape test, described in ASTM D3359. For this test an unpatterned metal film is either transferred-by-polymerization onto the SMP substrate or fabricated through metal evaporation directly onto a premade substrate. The level of adhesion to the substrate is quantified by the amount of delamination witnessed, with 5B indicating no delamination and 0B indicating large-scale delamination. As seen in Table 1, all samples with a chromium adhesion layer prepared by the process showed no delamination both as dry samples and after swelling in PBS for 10 days. Direct metal deposition led to moderate to good adhesion in the dry state, but nearly complete delamination after swelling for 10 days for samples containing AA. Very poor adhesion was observed if no chromium adhesion layer was used with the polyacrylate systems regardless of method. The level of swelling increases with AA content.

Neural interfaces have traditionally been made of materials with moduli 5-9 orders of magnitude stiffer than neural tissue. In this work, SMP cortical recording electrodes fabricated and inserted in the high modulus state soften three orders of magnitude due to a combination of thermal stimuli and plasticization by water uptake. Demonstration of a modular transfer-by-polymerization process for the manufacture of SMP-based flexible electronic devices requires control over electrode patterning, substrate synthesis, subsequent lithography and final device performance. The process developed in this work provides much of this modularity. Conductor patterning is only limited by the constraints of photolithography on the sacrificial substrate. Substrate properties and conductor-polymer interactions are dictated by starting monomer chemistry which can vary widely based on commercially or synthetically available monomers.

Photolithography is used in two distinct processing stages: first, to pattern devices on the initial sacrificial substrates and second, to encapsulate and define recording sites on manufactured devices. The second, device encapsulation and recording site definition by photolithography of Parylene-C, occurs with the physiologically responsive, softening polymer as the substrate. As such, certain basic requirements on substrate properties were established to enable this processing. This stage requires temperature exposure of up to 40° C., to bake the photoresist, but no more to shift the substrate through its dry $T_g$ during processing. Due to the large difference in coefficient of thermal expansion of polymers above $T_g$ and the thin film metals used in this study, all substrates were kept below dry $T_g$ to prevent cracking of the electrode. A target dry $T_g$ was determined to be 60° C. to provide a safety factor for device fabrication. A system of copolymers containing 10 wt % of different hydrophilic monomers was established with very similar $T_g$ (±3° C.), as shown in FIG. 2A to 2B. This constant $T_g$ allows for identical dry processing conditions for devices irrespective of the selected monomers. Despite the similarity in dry thermomechanical properties, AA-containing polymers showed significant softening in physiological conditions as seen in FIG. 2C. While the 10 wt % AA sample begins to soften at 37° C. in PBS, the body temperature modulus is still more than 3 orders of magnitude stiffer than brain tissue. Water-loss does occur during testing, but the utilized method allows for elucidation of trends in thermomechanical properties of these polymers during simulated implantation.

Increasing the concentration of AA, in the monomer solution, yields substrates with a higher degree of plasticization following implantation. The basic condition that the dry substrates must remain in the glassy state below 50° C. was maintained for processing reasons. The $T_g$ as measured by DSC generally increases with AA content. DMA indicates the breadth and location of the transition is relatively unaffected by introduction of AA, and that all samples behave in a glassy manner below 50° C. After 1 day immersion in PBS, a stark contrast between the mechanical responses of the samples was noted. The modulus at body temperature decreases strongly with AA content. One day immersion in PBS was insufficient for the modulus of the samples to equilibrate; significant softening continues over the first week as shown in FIGS. 3A to 3B. Samples containing 15 wt % AA or greater showed slight stiffening over a month after the initial desired precipitous drop in modulus. This delayed stiffening effect (of approx. 1 MPa) has been reported previously in acrylate copolymers similar to the polymers studied here. The exhibited physiological modulus is due to both substrate plasticization by PBS and the temperature. The extent of substrate swelling will have a direct effect on the electrical properties of fabricated devices. There is an applied strain to the thin film metals induced by the change in volume of the substrate that can lead to electrode failure. Devices fabricated on the control substrate (25 wt % MA, 75 wt % IBoA) showed nominal change in resistance for a period up to 3 months, while devices fabricated on substrates with 20% AA lost electrical continuity after 24 hours due to the large change in volume. Future work will study how electrical properties change with the swelling profile of the substrate and how mechanical design can improve the recording fidelity of devices over time.

While substrate softening and compatibility with further processing are important factors in the determination of the basic viability of the studied system, understanding the interface between the metallic electrode and polymeric substrate is necessary to understand device durability. The specific parameter of interest is the adhesion of the electrode to the substrate. Polymer substrates are often chemically modified after polymerization to introduce oxygen-containing functional groups to increase adhesion. When a polymer is polymerized directly onto a surface as in the described transfer process, the high mobility in the monomeric state allows for formation of the most favorable interaction, both mechanically and chemically, with the electrode. The transfer-by-polymerization process allows for this interaction to form and then be locked into place by virtue of the polymerization. The chosen monomers already contain ether, ester and carboxylic acid functionalities with a high tendency of adhesion to the oxidized chromium adhesion layer as compared to the carbon-carbon polymer chains. In addition to the tendency for chromium to adhere to polymers with polar functionalities on the surface, it also adheres well to gold. Table 1 shows the ASTM D3359 swelling and adhesion tape test results by comparing the transfer-by-polymerization process and direct metal deposition. The results in Table 1 indicate that the effects of these factors on the adhesion of an unpatterned metal film were substantial. All samples processed by the transfer-by-polymerization method achieved the highest score provided by the ASTM both in the dry state and after immersion in PBS for 10 days. Samples processed using direct metal deposition exhibited moderate adhesion in the dry state, but all AA-containing samples exhibited near-complete delamination after PBS immersion.

| Composition | Swelling (%) | Transfer-by-Polymerization | | Direct Metal Deposition | |
|---|---|---|---|---|---|
| | | Dry | 10 Days Swelling | Dry | 10 Days Swelling |
| 25.0% MA 75.0% IBOA | 3.4 ± 0.4 | 5B | 5B | 4B | 3B |
| 10.0% Acrylic Acid | 15.4 ± 0.4 | 5B | 5B | 3B | 0B |
| 15.0% Acrylic Acid | 195.5 ± 13.8 | 5B | 5B | 5B | 0B |
| 17.5% Acrylic Acid | 216.5 ± 12.5 | 5B | 5B | 4B | 0B |
| 20.0% Acrylic Acid | 326.1 ± 9.7 | 5B | 5B | 2B | 0B |
| 25.0% MA 75.0% IBOA* | — | 0B | 0B | 0B | 0B |

Cortical recording probes could not be directly tested for adhesion based on ASTM D3359. Most electrodes based on thin films are made by deposition and patterning on top of a substrate, as is demonstrated on the sacrificial substrate in FIG. 4A. FIG. 4B shows that after transfer the polymer substrate and electrode share the same top plane. This increases the path tortuosity of a delaminating crack and should also improve observed device-substrate adhesion.

Cortical recording probes were fabricated using the described transfer-by-polymerization process, with a minimum feature size of 15 µm. This feature size could be markedly decreased in more advanced generations and is not a fundamental limitation of the process itself. The devices served as functional recording devices on acute timescales. Signal-to-noise ratios above the generally accepted threshold of 5 to 1 were achieved. While initial investigation has focused on cortical recording devices, a number of other neural biotechnology devices ranging from in vitro multielectrode arrays to nerve cuff electrodes to processing conditions. Several key challenges remain that limit device implementation. These devices need to be sterilized for implantation; for this work, 254 nm UV light was used for this purpose. However these substrates are strongly affected by isopropanol and cannot withstand autoclave temperatures leading to device disfiguration. Temperatures well above 40° C. are also useful in making reliable, low-resistance electrical contact to the device. Currently research is focused on overcoming these and other limitations using alternate electrode materials, both inorganic and organic, and exploring other polymer systems. These changes can be made readily without reinventing the basic concept of the transfer process as described.

The produced cortical probes soften post-insertion to more closely match the modulus of cortical tissue. Devices are fabricated using a transfer-by-polymerization process that allows for full-photolithographically defined electrodes on temperature and solvent sensitive substrates. Also utilized are the inherently available polar function groups in the chosen system to greatly increase adhesion as compared to traditional methods. This process is modular and will allow for tuning of substrate chemistry and electrode design for future improvements in various nervous system interfaces and in the broader field of flexible and stretchable electronics.

Methods

Materials and Methods:

Methyl acrylate (MA), isobornyl acrylate (IBoA), 2-hydroxyethyl acrylate (2HEA), 2-hydroxyethyl methacrylate (2HEMA), acrylic acid (AA), mono-2-(Methacryloyloxy) ethyl succinate (succinate), poly(ethylene glycol)diacrylate ($M_n$~575), phosphate buffered saline (PBS) and 2,2-dimethoxy-2-phenyl acetophenone further purification. All processing steps except polymer synthesis were performed in a Class 10,000 cleanroom.

Sacrificial Substrate Preparation:

75×50 mm glass microscope slides were cleaned by subsequent steps of scrubbing in an Alconox solution, sonication in acetone, sonication in isopropanol and repeated as necessary until free of optically visible unwanted material. 500 nm of Parylene-C was deposited in a SCS Labcoter 2 (SCS Systems).

Metal Electrode Deposition and Patterning:

300 nm of Au and 50 nm of Cr were deposited, at 0.2 nm/min, using electron-beam evaporation without removing the sample from vacuum. Electrodes were then patterned by standard photolithography and etched using chromium etchant (CR-7S Cyantek Corporation) and gold etchant (AU-5 Cyantek Corporation). For adhesion tests, AFM and XPS films were not patterned. To test direct metal deposition a previously synthesized polymer film (1 mm thick) was coated with 50 nm Cr and 300 nm Au.

Polymer Synthesis and Electrode Transfer-by-Polymerization:

The appropriate (meth)acrylate monomers, 1 wt % PEGDA and 0.1 wt % DMPA were mixed. The monomer solution was injected between two glass slides (75×50 mm) separated by a glass spacer, 1.2 mm or 35 µm thick. Polymerization was performed using a crosslinking chamber with five overhead 365 nm UV bulbs (UVP via Cole-Parmer) for 120 minutes. Device transfer was accomplished by using the sacrificial substrate with patterned electrodes or unpatterned film as the bottom slide for the mold. Due to the comparatively poor adhesion of the Parylene-C to the sacrificial glass slide devices and Parylene were transferred to the SMP substrate. Care was taken to ensure the bottom glass slide remained on the polymer substrate. oxygen plasma (50 W, 100 mTorr, 6 min) was used to remove the sacrificial Parylene-C layer. RIE was performed with a Technics RIE in intervals of 30 s on and 15 s off to prevent significant device heating. Another layer of 500 nm thick Parylene-C was deposited under the same conditions. This layer was patterned using photolithography, while limiting the resist bake temperature to 40° C. After Parylene-C etching with RIE under the same conditions, residual photoresist (S1813 Shipley) was removed by a flood exposure and developing. Recording sites were approximately 300 µm$^2$ in area.

Device Definition and Electrical Bonding:

Cortical probes were cut from the surrounding polymer sheet using a $CO_2$ laser. Final shank width was approximately 0.5 mm. Devices were removed from the carrier glass slide by lifting gently with a moistened razor blade. Probes were electrically bonded to a custom printed circuit board using an anisotropic conductive adhesive (Sunray Scientific) based on magnetically alignable particles in a polymer matrix. Devices for implantation were sterilized by exposing to 254 nm UV light for 3 hours.

Dynamic Mechanical Analysis:

DMA was performed on a Mettler Toledo DMA 861e/SDTA. Samples were cut into cylinders approximately ~1 mm thick and ~3 mm in diameter. The mode of deformation was shear, and strain was limited to a maximum of 0.3%. Samples were tested at a heating rate of 2° C./min. A multiplexed frequency mode was run on all samples in which 1, 2, 5 and 10 Hz deformation occurs simultaneously; the frequency of deformation shown is 1 Hz. Tests were conducted in a nitrogen atmosphere. DMA on swollen samples was performed by immediately removing a swollen sample and testing in shear parallel-plate configuration. In this configuration approximately 70% of the This method was selected as it is appropriate for both swollen samples and for explanted samples. Comparison of in-vitro and in-vivo immersed samples is an area of continuing work. While this method does permit some water loss during testing it provides a conservative estimate of the modulus drop of the polymer in physiological conditions. It should be noted that all samples that were swollen were chosen to be appropriately sized for mechanical testing (~1 mm thick) and are not representative of the dimensions of a cortical probe (~35 μm thick). $T_g$ by DMA is denoted as the peak of tan δ. Each composition was tested twice. The value of the y-intersect for all DMA data presented in this work was chosen to be 10 kPa, approximately the modulus of brain tissue, to maintain the awareness of the reader to the target modulus for the lowest mechanical mismatch.

Differential Scanning Calorimetry:

DSC was performed on a Mettler Toledo DSC 1 with an intracooler option. Samples were heated from room temperature to 100° C., cooled to −50° C., and subsequently heated to 200° C. Data shown are of only the second heating ramp. All heating and cooling rates were fixed at 10° C./min. Tests were conducted in a nitrogen atmosphere. $T_g$ by DSC is denoted as the midpoint of the transition.

X-Ray Photoelectron Spectroscopy:

XPS measurements were done on a PHI 5800 spectrometer equipped with an Al Kα monochromated X-ray source. A take-off angle of 90° from the surface was employed. Spectra were recorded with 29.35 eV pass energy, at 0.125 ev/step. The peak locations were corrected on the basis of the C—C (1s) binding energy of 284.5 eV. XPS peak assignments were made based on detailed, self-consistent curve fitting of the recorded spectra using Voigt line shapes in conjunction with a Shirley background subtraction. Veeco, Model 3100 Dimension V Atomic Probe Microscope in tapping mode. An area of 25 μm$^2$ was scanned at a rate of 1 Hz with a 1 Ohm Si probe with $f_0$=320-359 kHz and k=12-103 N/m. Three measurements were made per sample.

Scanning Electron Microscopy:

Scanning electron microscopy was performed in a ZEISS SUPRA-40. Samples were sputtered with gold to reduce charging effect. Images were captured in a 52° angle; at a working distance and electron high tension of 11 mm and 7 KeV respectively.

Adhesion Testing:

Adhesion Testing was performed in accordance with ASTM D3359. A crosshatch pattern was scored through the thin metal film to the substrate. A pressure-sensitive tape (SEMicro CHT) was applied to the area of the crosshatch, formed by six parallel cuts and six perpendicular cuts (1 mm dimension squares). The tape was removed quickly at an angle close to 180°. The level of adhesion was quantified by the percentage of the remaining metal coating on the polymer substrate. The scale defined by the standard is: 5B—0% of coating removed, 4B—Less than 5% removed, 3B—5-15% removed, 2B—15-35% removed, 1B—35-65% removed, 0B—Greater than 65% removed.

Acute Neural Recording:

Rats were anaesthetized by IP injection, heads fixed in a stereotaxic frame, and the somatosensory cortex exposed. Electrodes were lowered under micromanipulator control until neural activity was evident on an oscilloscope, then electrodes were inserted a further 800 μm. Electrodes rested undisturbed for 5 min, then spontaneous neural activity was recorded with a 16-channel Recording System (Plexon). All experimental procedures were performed in accordance with the National Institutes of Health Guide for the and Use Committee.

What is claimed is:

1. A method for adhering a metal layer to a polymer substrate, comprising:
    depositing the metal layer on a sacrificial substrate of a mold to form part of an interior surface of the mold;
    depositing a solution of monomers on the metal layer, wherein:
        the solution of monomers consists of: a free radical initiator, thiol monomers with two or more thiol functional groups, and, vinyl monomers with two or more vinyl functional groups, acrylate monomers with two or more vinyl functional groups, acrylate monomers with two or more vinyl functional groups and acrylate co-monomers with one vinyl functional group, or with both the vinyl monomers and the acrylate monomers, and
        a total number of the thiol functional groups and a total number the vinyl functional groups are in stoichiometric imbalance such that the total number of the thiol functional groups exceeds the total number of the vinyl functional groups to provide an excess of the thiol functional groups; and then
    polymerizing the monomers together in the presence of the metal layer such that the thiol monomers and the vinyl monomers in the solution of monomers on the metal layer are polymerized together to form the polymer substrate on the metal layer and wherein the polymer substrate is chemically adhered to the metal layer; and then
    removing the polymer substrate from the mold such that the metal layer is removed from the mold and adhered to the polymer substrate.

2. The method according to claim 1, wherein the metal layer includes a layer of gold, iridium oxide, titanium nitride, or titanium oxide.

3. The method according to claim 2, wherein the metal layer includes the layer of gold located on a layer of aluminum, chromium or titanium.

4. The method according to claim 1, wherein the polymerizing of the monomers together forms the polymer substrate that is a thiol-ene polymer.

5. The method according to claim 1 wherein, the metal layer is lithographically patterned prior to the depositing of the solution of monomers on the metal layer of the mold.

6. The method according to claim 1 wherein, the mold is a blend of radiation crosslinked thermoplastic polymer and a polyunsaturated monomer, or, an epoxy or siloxane.

7. The method according to claim 1, wherein the polymerizing of the monomers together to form the polymer substrate includes forming a partially polymerized polymer substrate.

8. The method according to claim 7, wherein the partially polymerized polymer substrate is deformed into a different shape, and then, the polymerizing of the monomers together to form the polymer substrate is completed.

9. The method according to claim 1, wherein the acrylate co-monomers with the one vinyl functional group in the solution of monomers includes methyl acrylate and isobornyl acrylate crosslinked with the acrylate monomers with two or more vinyl functional groups of poly(ethylene glycol) diacrylate.

10. The method according to claim 9, wherein the acrylate co-monomers with the one vinyl functional group in the solution of monomers includes 2-hydroxyethyl acrylate, 2-hydroxyethyl methacrylate (2HEMA), acrylic acid or mono-2-(Methacryloyloxy)ethyl succinate.

11. The method according to claim 1, wherein the acrylate co-monomers with the one vinyl functional group in the solution of monomers includes acrylic acid.

12. The method according to claim 11, wherein the acrylic acid in the solution of monomers is in a concentration range from 10 wt % to 20 wt %.

\* \* \* \* \*

UNITED STATES PATENT AND TRADEMARK OFFICE
CERTIFICATE OF CORRECTION

| | |
|---|---|
| PATENT NO. | : 11,013,835 B2 |
| APPLICATION NO. | : 14/376352 |
| DATED | : May 25, 2021 |
| INVENTOR(S) | : Taylor Ware and Walter Voit |

It is certified that error appears in the above-identified patent and that said Letters Patent is hereby corrected as shown below:

In the Specification

In Column 1, Lines 11-19, delete "STATEMENT REGARDING FEDERALLY-SPONSORED RESEARCH OR DEVELOPMENT This invention was made with government support under Grant No. 2011113646 awarded by the National Science Foundation and with FUSION support from the State of Texas. The government has certain rights in the invention." and insert --STATEMENT OF GOVERNMENT INTEREST This invention was made with government support under Grant No. DGE1147385 awarded by the National Science Foundation. The government has certain rights in the invention.--

Signed and Sealed this
Twenty-fourth Day of October, 2023

Katherine Kelly Vidal
*Director of the United States Patent and Trademark Office*